(12) United States Patent
Dell'oca

(10) Patent No.: US 7,823,296 B2
(45) Date of Patent: Nov. 2, 2010

(54) DEPTH GAUGE

(75) Inventor: Alberto A. Fernandez Dell'oca, Montevideo (UY)

(73) Assignee: Synthes USA, LLC, West Chester, PA (US)

( * ) Notice: Subject to any disclaimer, the term of this patent is extended or adjusted under 35 U.S.C. 154(b) by 0 days.

(21) Appl. No.: 12/501,934

(22) Filed: Jul. 13, 2009

(65) Prior Publication Data

US 2009/0272001 A1 Nov. 5, 2009

Related U.S. Application Data

(63) Continuation of application No. 11/248,525, filed on Oct. 13, 2005, now Pat. No. 7,559,150.

(51) Int. Cl.
*A61B 5/107* (2006.01)
(52) U.S. Cl. .............................. 33/512; 33/783; 600/587
(58) Field of Classification Search ................... 33/512, 33/783, 806, 810, 811, 832, 833, 836
See application file for complete search history.

(56) References Cited

U.S. PATENT DOCUMENTS

| 5,013,318 | A  | * | 5/1991  | Spranza, III      | 33/512  |
|-----------|----|---|---------|-------------------|---------|
| 6,802,817 | B2 | * | 10/2004 | Baxter-Jones et al. | 600/587 |
| 7,559,150 | B2 | * | 7/2009  | Fernandez         | 33/512  |
| 2005/0066535 | A1 | * | 3/2005 | Rupp et al.       | 33/512  |
| 2008/0306408 | A1 | * | 12/2008 | Lo                | 600/587 |
| 2009/0049705 | A1 | * | 2/2009 | Kim               | 33/512  |

* cited by examiner

*Primary Examiner*—G. Bradley Bennett
(74) *Attorney, Agent, or Firm*—Fay Kaplun & Marcin, LLP

(57) ABSTRACT

A depth gauge for measuring the depth of blind holes in bones and/or nails inserted into bones. The measurement tool comprises: a probe with an abutment at its end to engage against the distal edge of the blind hole; a tubular body; and a grooved insert. After the probe, lying into the tubular body, is positioned through the blind hole to be measured, the grooved insert is slid forward inside the tubular body, surrounding the probe, and pushing the probe sideward, towards the blind hole wall. When probe and groove insert are retracted together, they firmly engage against the distal bone wall. The tubular housing is then pushed forward until it abuts against the proximal bone wall, allowing even in small diameter holes, an accurate reading of hole depth on the scale located at the rear end of the probe.

18 Claims, 6 Drawing Sheets

Ja# DEPTH GAUGE

PRIORITY CLAIM

The present application is a Continuation Application of U.S. patent application Ser. No. 11/248,525 filed on Oct. 13, 2005 entitled "Depth Gauge." The disclosure of this application is incorporated herein by reference.

FIELD OF THE INVENTION

The present invention relates to measurement devices, and, more particularly, to depth gauges for determining the depth of holes in bone and/or orthopedic implants inserted into bone.

BACKGROUND OF THE INVENTION

It is often necessary to exactly assess the depth of a blind hole. Existing measurement devices have a single hook on one end of a calibrated rod. The rod is inserted through the hole, and after the hook emerges through the opposite, distal wall, the rod is retracted until it abuts against the blind edge of the hole. The disadvantage of these devices is that hooking the edge of the hole through the far wall could be quite difficult, mainly when measuring smaller diameter holes.

For the foregoing deficiencies in the prior art, a new hole depth-measuring instrument that provides a fast and accurate measure is needed. There is a further need to have an instrument wherein the probe firmly engages to the distal edge of the hole, allowing a precise measurement of the depth of a blind hole.

SUMMARY OF THE INVENTION

Accordingly, it is an object of the present invention to provide a simple and effective tool to measure the depth of a blind hole.

Another object of the invention herein is to provide an instrument wherein the probe firmly engages to the distal edge of the hole, allowing a precise measurement of the depth of a blind hole.

A preferred embodiment of the present invention comprises a probe which has opposed proximal and distal ends, wherein a scale located at the proximal end of the probe defines an axis and presents indicia along the axis, and the probe has an abutment at its distal end; a tubular housing which is slidably mounted on the scale located on the probe; and a grooved insert which has opposed proximal and distal ends. The distal end of the grooved insert tapers to a sharp edge.

By fulfilling the previously mentioned objects, the present invention is extremely helpful to the medical care area.

Other objects, advantages and novel features of the present invention will become apparent from the following detailed description of the preferred embodiments when considered in conjunction with the accompanying drawings.

BRIEF DESCRIPTION OF THE DRAWINGS

Preferred embodiments of the present invention are disclosed in the accompanying drawings, wherein similar reference characters denote similar elements throughout the several views, and wherein.

DETAILED DESCRIPTION OF THE PREFERRED EMBODIMENTS

Hereinafter, a preferred embodiment of the present invention will be described with reference to FIGS. 1-2.

Figure 1:
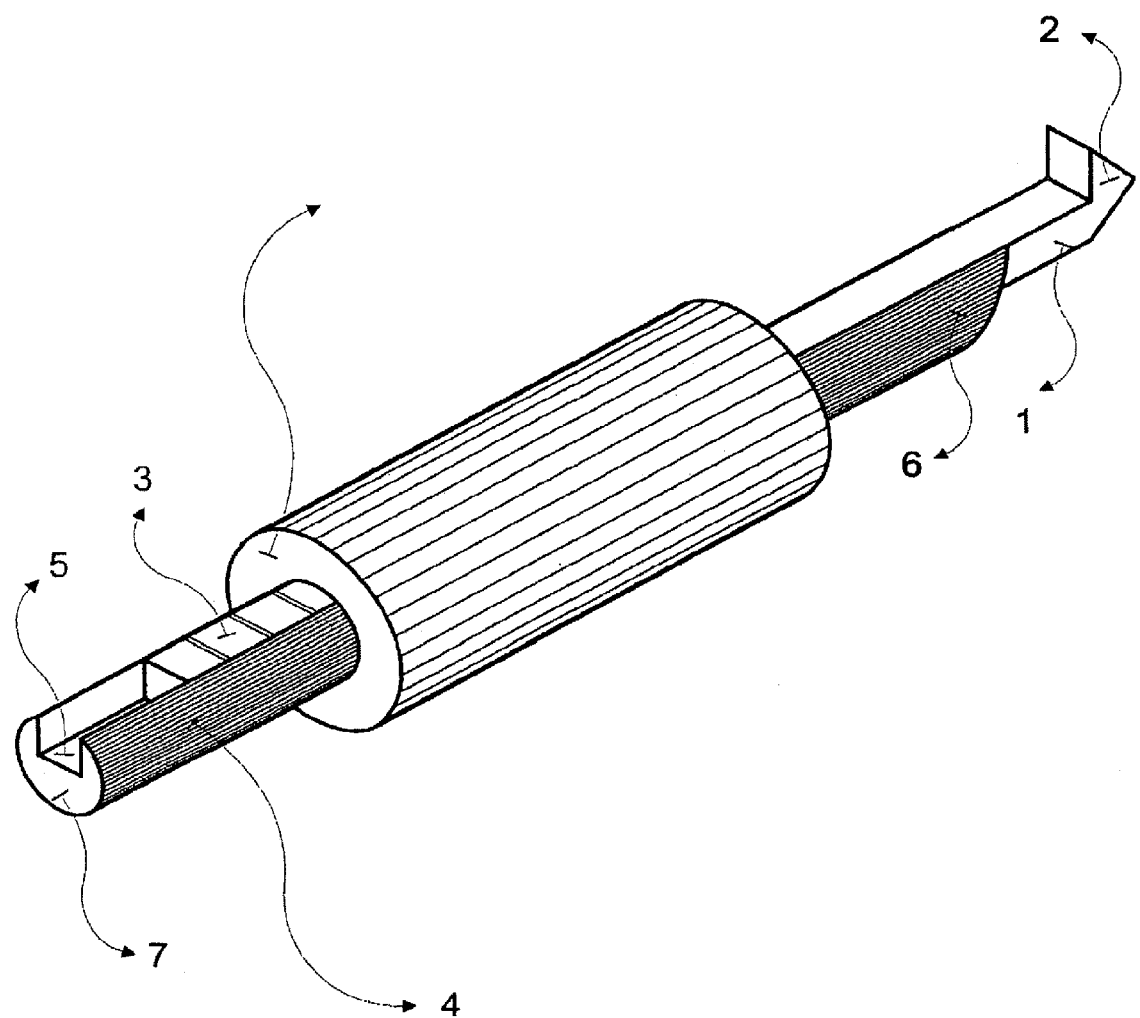
FIG. 1 is a perspective view of a preferred embodiment of the depth gauge system of the present invention.

FIG. 1 shows a preferred embodiment of a depth-measuring tool of the present invention. A probe 1, engaged with groove 5 of a grooved insert 4, is able to slide freely with respect to the grooved insert 4 along the longitudinal axis of the probe 1. The tubular housing 8 is slidably mounted over probe 1 and grooved insert 4.

Figure 2:
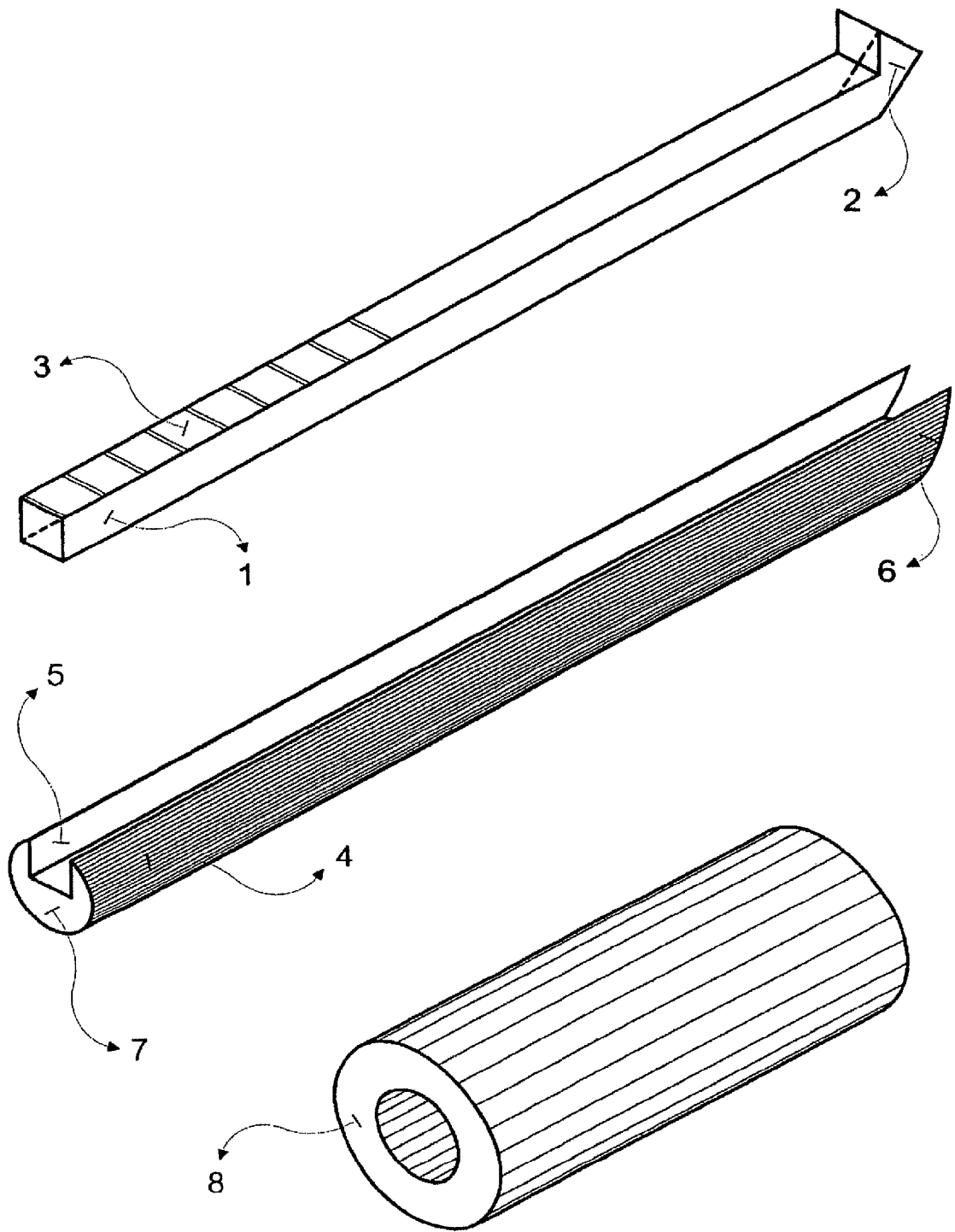
FIG. 2 is a perspective view of the disassembled depth gauge system shown in FIG. 1.

The disassembled system is clearly seen in FIG. 2, wherein its three components are shown: the probe 1; the grooved insert 4; and the tubular housing 8. The probe has an abutment 2 on its distal end and a scale 3 located at its proximal end. The grooved insert 4 includes a groove 5 to accommodate the probe 1, a proximal end 7, and a tapered distal end 6 designed to avoid impingement against the proximal border of the hole to be measured 10. The tubular housing 8 is sized to accommodate the grooved insert 4 and the probe 1 inside it.

In another preferred embodiment, probe 1 may include a male thread on its proximal end configured to receive a female threaded device, such that the female threaded device may be used to push tubular housing 8 against the proximal bone wall while allowing the scale 3 to mark the exact position of the nail being targeted.

Hereinafter, a preferred method of depth measuring according to a preferred embodiment of the present invention will be explained with reference to FIGS. 3-6.

Figure 3:
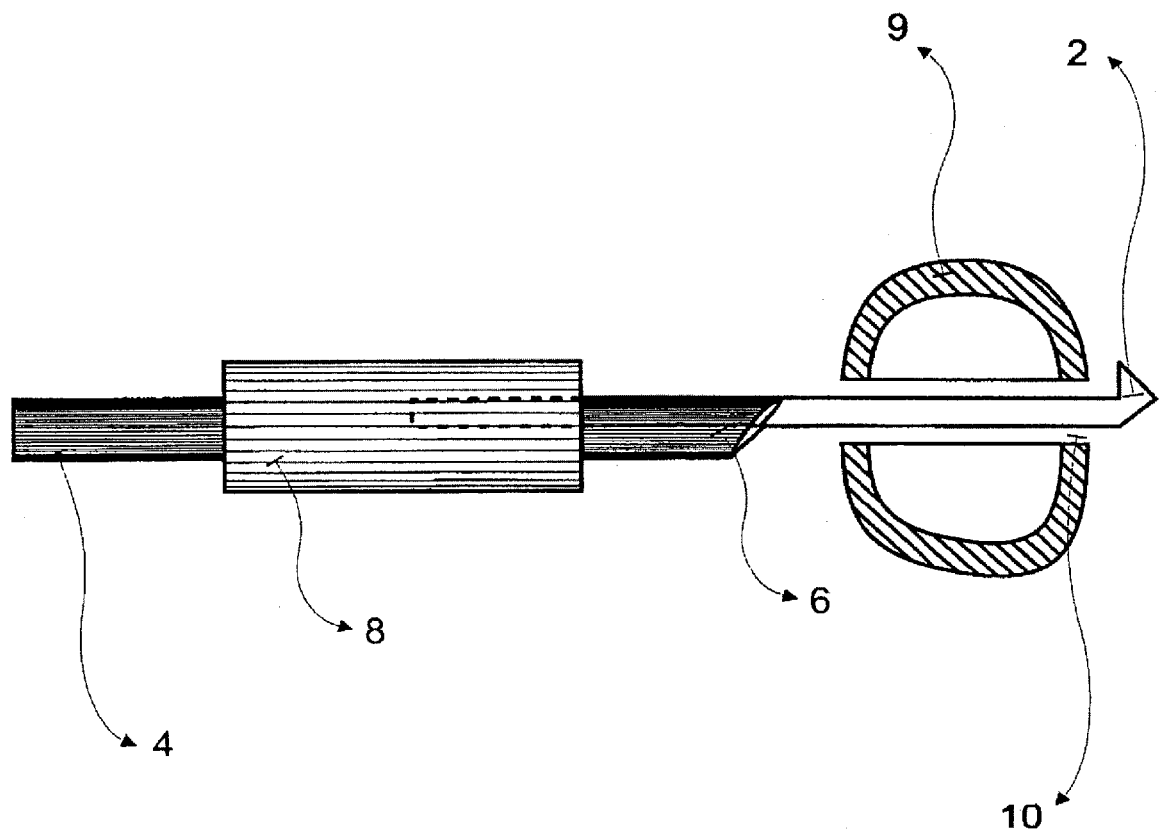
FIG. 3 is a side view of a first step in a preferred surgical technique employing the depth gauge system shown in FIG. 1.

When the grooved insert 4 is retracted, the probe 1 is easily inserted into and through the bone hole 9, while the tubular housing 8 lies to the back, as best shown in FIG. 3.

Figure 4:
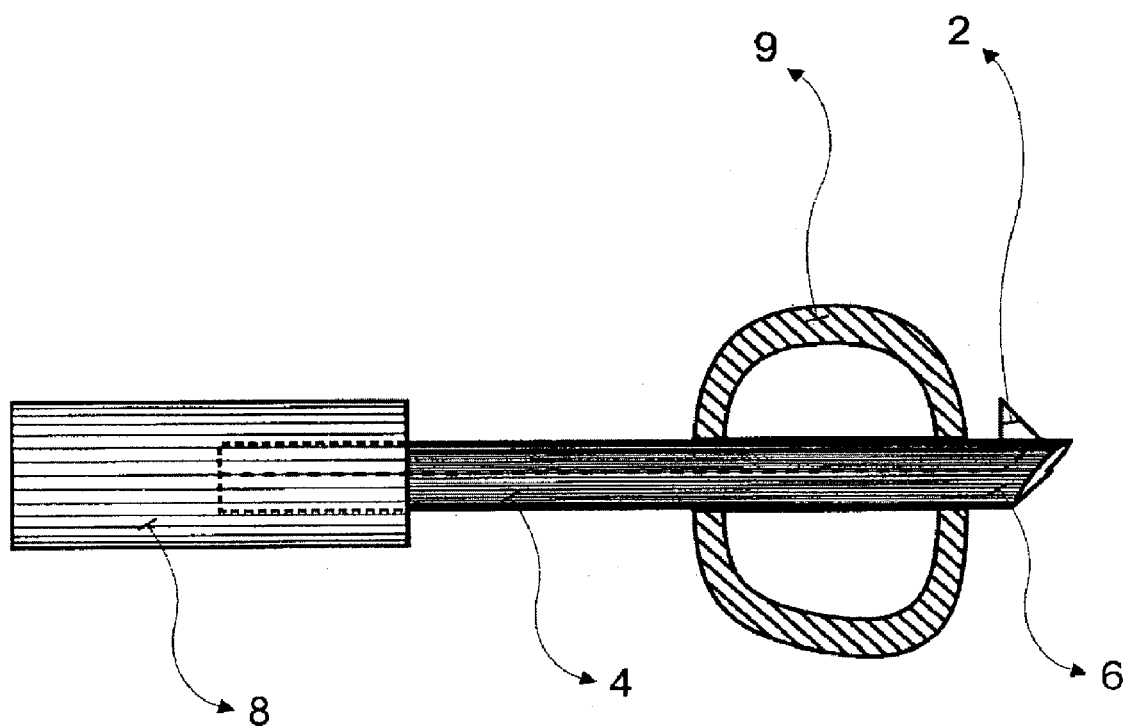
FIG. 4 is a side view of a second step in a preferred surgical technique employing the depth gauge system shown in FIG. 1.

The grooved insert 4 is then slid forward to its final destination pushing the probe 1 upward, towards the upper bone hole wall 10, as clearly shown in FIG. 4. The tapered distal end 6 of the grooved insert 4 prevents the grooved insert 4 from abutting against the bone hole wall 10.

Figure 5:
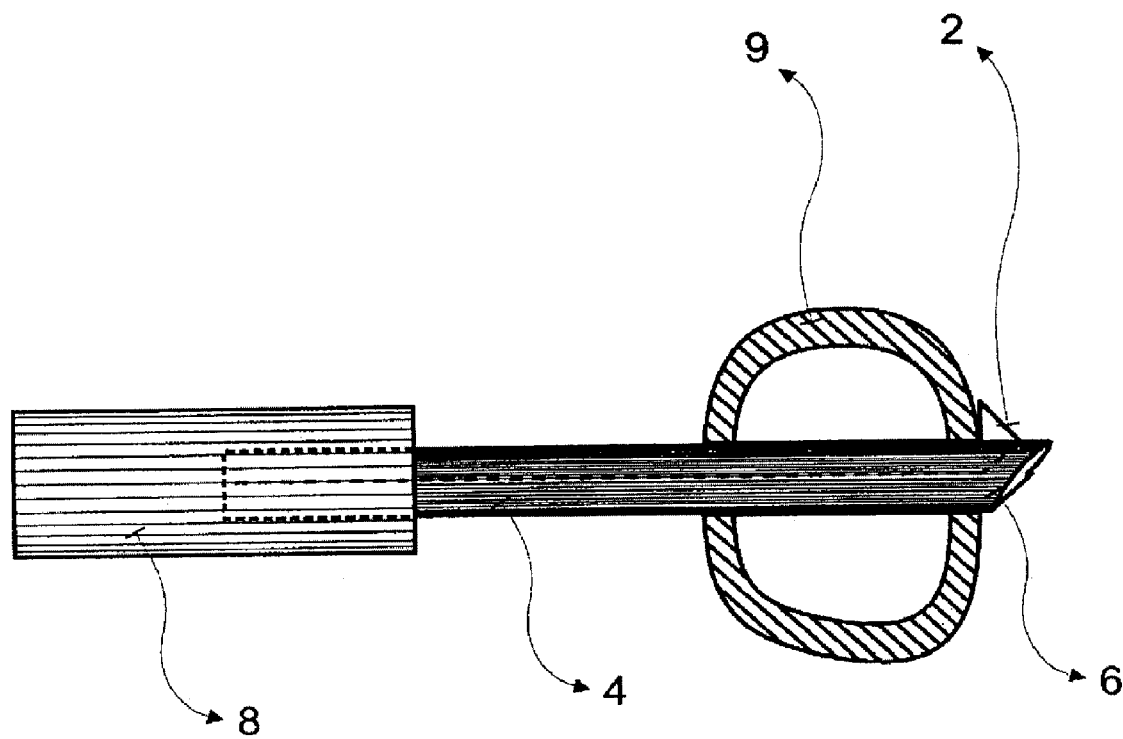
FIG. 5 is a side view of a third step in a preferred surgical technique employing the depth gauge system shown in FIG. 1.

When the probe 1 and the grooved insert 4 are retracted together with respect to the bone 9, the abutment 2 at the probe 1 firmly engages against the distal bone wall as shown in FIG. 5.

Figure 6:
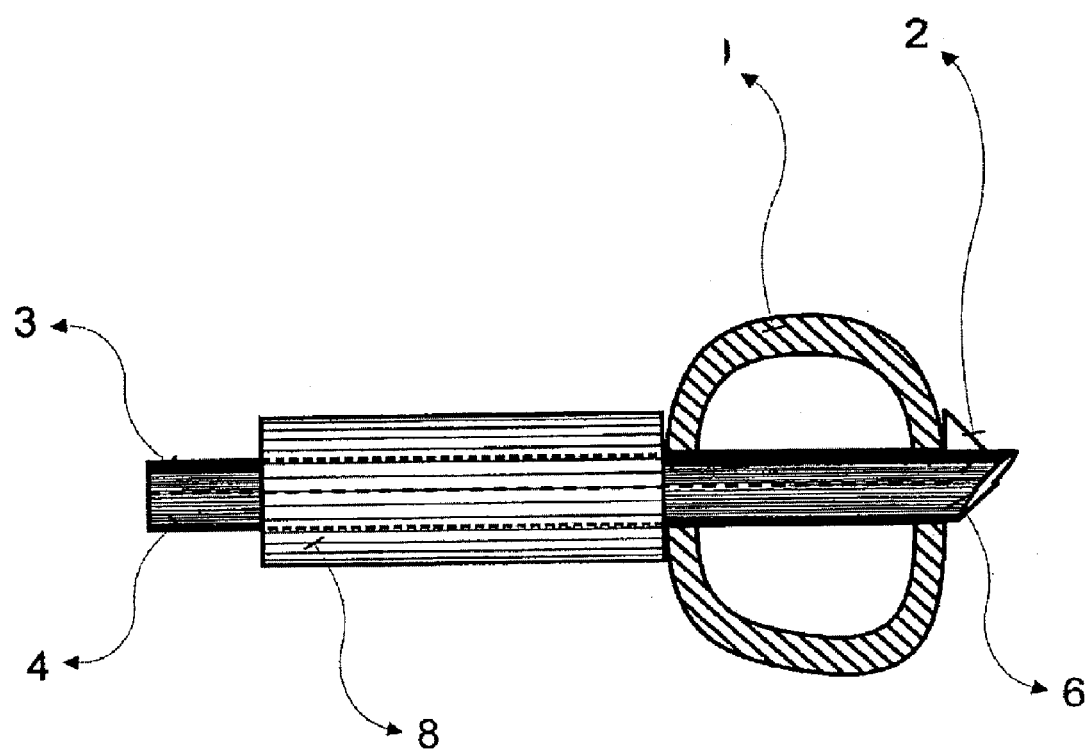
FIG. 6 is a side view of a fourth step in a preferred surgical technique employing the depth gauge system shown in FIG. 1.

FIG. 6 shows the final step of the measurement procedure. The tubular housing 8 is pushed forward until it abuts against the proximal bone wall, allowing an accurate reading of hole depth on the scale 3 located at the rear end of the probe 1.

While a preferred embodiment of the invention has been illustrated and described, it will be understood that those skilled in the art will thereby be enabled to devise variations and modifications without departing from the spirit and scope of this invention, as defined in the appended claims.

What I claim as my invention is:

1. An instrument for measuring blind holes in one of (a) bones and (b) implants inserted within bones, comprising:
   a. an elongated probe having a proximal end, a distal end, a longitudinal axis, and a scale on the proximal end of the probe;
   b. a housing slidably mounted relative to the scale and having a length that is less than a length of the elongated probe;
   c. an abutment formed at the distal end of the probe, the abutment configured and dimensioned to fit through a hole to be measured; and
   d. an elongated insert having a longitudinal groove for receiving the probe in a sliding engagement with respect thereto,
   wherein a retraction of the insert in a direction away from the hole causes movement of the abutment toward a distal wall adjacent the hole.

2. The instrument of claim 1, wherein a distal end of the insert includes a tapered portion.

3. The instrument of claim 1, wherein forward movement of the insert along the probe prevents simultaneous retraction of the probe and the groove from the hole.

4. The instrument of claim 1, wherein indicia extend along the scale on the proximal end of the probe to indicate the depth of the hole.

5. The instrument of claim 1, wherein the proximal end of the probe includes a threaded portion, and the instrument further comprises a threaded element that mates with the threaded portion at the proximal end of the probe.

6. The instrument of claim 5, wherein the threaded element is configured and dimensioned to push the housing against a proximal wall adjacent the hole.

7. The instrument of any claim 1, wherein both the probe and the insert slide within the housing.

8. The instrument of claim 1, wherein the housing is tubular.

9. The instrument of claim 2, wherein the distal end of the insert tapers to a sharp edge.

10. A method for measuring a depth of a blind hole in one of (a) bone and (b) implant inserted into a bone, comprising:
    a. providing a measurement tool including
       i. an elongated probe having a proximal end, a distal end, a longitudinal axis, and a scale on the proximal end of the probe;
       ii. a housing slidably mounted relative to the scale and having a length that is less than a length of the elongated probe;
       iii. an abutment formed at the distal end of the probe, the abutment configured and dimensioned to fit through a hole to be measured; and
       iv. an elongated insert having a longitudinal groove for receiving the probe in a sliding engagement with respect thereto
    b. inserting the distal end of the probe through the hole;
    c. sliding the insert toward the distal end of the probe such that the abutment moves toward a distal wall adjacent the hole;
    d. simultaneously retracting the probe and the grooved insert until the abutment at the distal end of the probe engages the distal wall adjacent the hole;
    e. moving the tubular housing against a proximal wall adjacent the hole; and
    f. reading a depth measurement from the scale located on the probe.

11. The method of claim 10, wherein a distal end of the insert includes a tapered portion.

12. The method of claim 11, wherein the distal end of the insert tapers to a sharp edge.

13. The method of claim 10, wherein forward movement of the insert along the probe prevents simultaneous retraction of the probe and the groove from the hole.

14. The method of claim 10, wherein indicia extend along the scale on the proximal end of the probe to indicate the depth of the hole.

15. The method of claim 10, wherein the proximal end of the probe includes a threaded portion, and the tool further comprises a threaded element that mates with the threaded portion at the proximal end of the probe.

16. The method of claim 15, further comprising the step of:
    a. advancing the threaded element along the threaded portion of the probe to secure the housing against a proximal wall adjacent the hole.

17. The method of claim 10, wherein both the probe and the insert slide within the housing.

18. The method of claim 10, wherein the housing is tubular.

* * * * *